(12) United States Patent
Santiago Fontaina

(10) Patent No.: US 8,978,980 B2
(45) Date of Patent: Mar. 17, 2015

(54) INTELLIGENT FIRST AID KIT

(76) Inventor: Jose Maria Santiago Fontaina, Ribeira (ES)

( * ) Notice: Subject to any disclaimer, the term of this patent is extended or adjusted under 35 U.S.C. 154(b) by 120 days.

(21) Appl. No.: 13/698,955

(22) PCT Filed: Nov. 5, 2010

(86) PCT No.: PCT/ES2010/070720
§ 371 (c)(1),
(2), (4) Date: Jan. 18, 2013

(87) PCT Pub. No.: WO2011/144770
PCT Pub. Date: Nov. 24, 2011

(65) Prior Publication Data
US 2013/0112590 A1 May 9, 2013

(30) Foreign Application Priority Data
May 19, 2010 (ES) .................. 201000548 U

(51) Int. Cl.
| G06K 7/10 | (2006.01) |
| A61F 17/00 | (2006.01) |
| G06F 19/00 | (2011.01) |
| A61J 1/03 | (2006.01) |
| A61J 7/00 | (2006.01) |

(52) U.S. Cl.
CPC .. *A61F 17/00* (2013.01); *A61J 1/03* (2013.01); *A61J 7/0084* (2013.01); *G06F 19/3462* (2013.01)
USPC .................. 235/462.01; 235/383; 235/462.13

(58) Field of Classification Search
USPC ................ 235/462.01, 462.13, 381, 385, 383
See application file for complete search history.

(56) References Cited

U.S. PATENT DOCUMENTS

| 4,967,928 | A | 11/1990 | Carter |
| 5,047,948 | A | 9/1991 | Turner |
| 5,314,243 | A | 5/1994 | McDonald et al. |
| 5,745,366 | A | 4/1998 | Higham et al. |
| 6,151,536 | A | 11/2000 | Arnold et al. |
| 6,330,491 | B1 | 12/2001 | Lion |
| 6,532,399 | B2 | 3/2003 | Mase |
| 2002/0100762 | A1 | 8/2002 | Liff et al. |
| 2006/0154642 | A1* | 7/2006 | Scannell, Jr. ............... 455/404.1 |
| 2008/0077274 | A1 | 3/2008 | Kim |

FOREIGN PATENT DOCUMENTS

| CN | 200984288 | 12/2007 |
| ES | 2 296 963 | 5/2008 |
| WO | WO 98/26746 | 6/1998 |
| WO | WO 03/071943 | 9/2003 |

OTHER PUBLICATIONS

International Search Report for International Application No. PCT/ES2010/070720 mailed May 9, 2011.

* cited by examiner

*Primary Examiner* — Karl D Frech
(74) *Attorney, Agent, or Firm* — Merchant & Gould P.C.

(57) ABSTRACT

Intelligent first-aid kit (1) includes of a fixed first-aid kit of the conventional first-aid kits for storing the most important drugs which it is important to have for emergencies or chronic illnesses. A parallelepipedal is container divided into several elongated compartments (2), preferably with a rectangular cross section and a vertical orientation, which includes a drawer (3), an input reader (5.1), an output reader (5.2), a slot (4) for the insertion of an electronic health card, a keypad (6), a screen (7) and a control module (8).

3 Claims, 1 Drawing Sheet

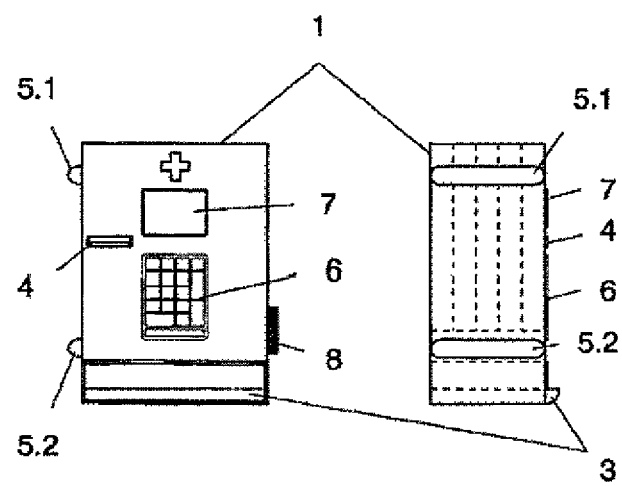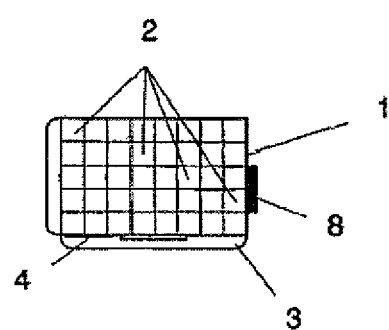

INTELLIGENT FIRST AID KIT

This application is a National Stage Application of PCT/ES2010/070720, filed 5 Nov. 2010, which claims benefit of Serial No. U201000548, filed 19 May 2010 in Spain and which applications are incorporated herein by reference. To the extent appropriate, a claim of priority is made to each of the above disclosed applications.

The object of the present invention is a first aid kit which allows a controlled monitoring of its content which, in addition to being very useful for its owner or administrator, can also be of great use to the doctor or organization responsible for providing medical care to said owner in his/her role as a patient.

Access to the first aid kit is generally restricted to its owner through a microchip integrated card and drug availability is such that any input or output of specifics is registered as the result of the existence of an electronic bar code reader.

The invention results in:
a) an accurate knowledge of the first aid kit content
b) a correct monitoring of the patient by his/her family doctor
c) a drug savings for public health administration since it provides a perfect control of the first aid kit content which allows preventing new prescriptions duplicating the drugs already existing in the first aid kit In an advanced general implementation phase, the inventor considers that this idea is of public interest due to the significance that it may entail for public health organization both at the local level and at the provincial, regional or even national levels because putting the invention into practice will allow managing those drugs which are no longer taken by the patient, either due to the change in the medical prescription or death. In these cases managing the remaining drugs will allow establishing a bank of deposit for the subsequent use thereof by other patients following the same treatment.

This resource optimization will without doubt lead to a more sustainable health system.

SECTOR OF THE ART OF THE INVENTION

The invention relates to the sector of human necessities, chapter of health, protection, amusements concerning medical sciences and public health leading to the design, production and supply of first aid kits for home use or even for small enterprises from a commercial view point.

BACKGROUND OF THE INVENTION

Today the existence of first aid kits in private homes, businesses, sport organizations, small, medium and large enterprises is not only advisable but required by the national, regional or local governments. It is also common for certain athletes, motorists, explorers, etc., to carry it with them to attend to small medical emergencies which require first aid care.

In other words, there are small first aid kits to fulfill the needs of easy transportation and other larger first aid kits which are normally fixed somewhere in the private home, the office or the related organization.

In these cases, there are inventions which allow removing the first aid kit from its fixing to the wall so that the first aid kit can be brought closer to the injured person or patient and not the other way around.

Other existing solutions relate to case-type first aid kits which are perfected in terms of its shape, its ease of transport and above all in terms of the inner organization of the drugs which it contains to maintain the order and the integrity of some fragile components.

Inventions relating to the device for closing the case or first aid kit generally to prevent unauthorized opening and content loss or theft can also be mentioned.

Another invention in the field of drug administration includes programmable devices for people with Alzheimer's disease. These devices are programmed by the caretaker and they automatically open at predetermined hours with light or acoustic alert signals so that the patient can be provided with the needed tablets at the right time.

These programmable devices are already available to the public, there being models which are duly protected under the Spanish Patent and Trademark Office.

What is not found today on the market is a first aid kit such as that presented herein which allows automatically controlling its content leading to knowing not only the amount and type of drugs available but also their expiration date at any time.

As seen below, the first aid kit presented has the significant advantage of knowing its exact content at all times; it further prevents drug waste since the family doctor can know the availability of a certain specific or any other specific with the same medicinal effects which can replace it by merely checking the kit.

As stated in the introduction, it is conceived that first aid kits of this type become sufficiently implemented at local, provincial, regional or national level so as to entail a true optimization of the health system relating to the advantageous use of drugs.

The authorities are already creating public awareness so that the drugs which are no longer needed or which have surpassed their expiration date are deposited in pharmacies or other drug collection points.

Suggestions for pharmaceutical companies to supply packagings with fewer tablets are also detected since it is proven that in many occasions patient only takes a small part of the content of each box.

Therefore it is considered that this invention involves a novel idea which will produce appreciable advantages to the people, organizations or countries deciding to use it.

SUMMARY OF THE INVENTION

The present invention relates to a newly conceived first aid kit incorporating a comprehensive electronic controller for controlling all the inputs and outputs of medicines. It has the particularity that the use thereof requires introducing the health card of the user through a slot prepared for such purpose. Said card, which has already become popular, consists of a card similar to bank cards, credit cards or debit cards, which incorporates an integrated circuit capable of permanently storing the medical history and parameters of a person.

In other words, to remove any drug from his/her own first aid kit, as the first step the user must introduce his/her health card and key in the private security number whereby the authorization for opening the first aid kit or automatically dispensing any of the products from that small drug storage will be produced.

Another feature of the invention lies on the fact that a bar code reader is installed inside the first aid kit which detects the type of drug passing in front of its sensor, the number of remaining units and its expiration date.

Finally there is a keypad with alphanumeric display which allows introducing certain data of the drugs or correcting possible defects.

All these elements are duly interconnected for correct operation resulting in the fact that the content and complementary information of the drugs existing in the first aid kit is permanently recorded in the microchip of the health card so that the doctor can known the health parameters of the user and the availability of stored drugs in non-routine or routine visits. If the doctor thinks that it is necessary to prescribe a certain specific, he will check whether or not such specific is in the first aid kit and he could even prescribe a drug having similar effects if it is available.

Redundant prescriptions are prevented with this system and drug consumption is optimized.

Regarding the content control, the simpler alternative is to hold the owner of the first aid kit responsible so that when he/she operates any box, either putting in or retrieving, the same systematically passes in front of the bar code reader. With this operation and in determined conditions of the packaging, the type of drug, the number of remaining pills or tablets and the expiration date can be controlled.

In another more advanced alternative, the first aid kit is equipped with a drug dispensing channel for its consumption with a bar code reader which automatically reads the content when the box passes in front of it, and another receiving channel for refilling which is also provided with another reader. There may be several ways for carrying this solution into practice but the way proposed is that which the first aid kit is compartmentalized in the horizontal or vertical direction in as many channels as the types of drugs to be stored.

Therefore the responsibility of making input or output readings is derived from the first aid kit itself with complete assurance in terms of the number and nature of the drugs it contains.

BRIEF DESCRIPTION OF THE DRAWINGS

A drawing with the following meaning is included:
FIG. 1 schematically depicts in three orthogonal views, including plan view, elevational view and profile view, a basic shape of the first aid kit.

The following is indicated:
1.—first aid kit
2.—compartment
3.—drawer
4.—slot
5.1.—input reader
5.2.—output reader
6.—keypad
7.—display
8.—control module

DESCRIPTION OF A PREFERRED EMBODIMENT

The intelligent first aid kit (1) (FIG. 1) consisting of a first aid kit of the conventional types for storing the most important drugs which one should have at home, in the office, factory, shop, etc., according to an embodiment preferred by the inventor is characterized in that the box of the first aid kit (1) is divided into several elongated compartments (2) preferably with a rectangular cross section, with a vertical orientation, each of them intended for storing one or several boxes or medicinal products which can be introduced in a specific position in each compartment (2). The first aid kit (1) is designed such that the boxes of drugs can only be introduced into the compartments (2) through the upper part and they can exit by gravity only through the lower part where there is a receiving drawer (3) facilitating drug collection. The flow of drugs in the opposite direction is not possible.

The first aid kit (1) is equipped with an input reader device (5.1) of those which identify the products depending on the bar codes incorporated in the box thereof in its upper left (or right) side.

Similarly and complementarily, it is equipped with an output reader (5.2) identical to the one above located in the lower left (or right) side of the first aid kit (1).

Furthermore, the first aid kit (1) has a slot (4) in its front part, although it can be located at any other location, through where the health card of the owner of the first aid kit can be introduced, the card being those which are provided with a microchip which can permanently store endless data by way of electronic archive.

The first aid kit (1) is also equipped with a keypad (6) and a display (7) in the front part although they can be located in a different location.

Finally a control module (8) with an internet connection is located in the right side or in any other place.

With this arrangement where all the electronic devices are interconnected to one another, the operation of the first aid kit (1) is simple as described below.

It should be pointed out that the dimensions of each compartment (2) with a vertical orientation must be defined depending on the boxes of drugs to be stored therefore filling a drug by mistake into a compartment for which it is not assigned can be prevented.

Filling the first aid kit with the chosen specifics must be done first. To that end it is essential to introduce the health card through the slot (4) pressing on the keypad (6) the security code corresponding to the owner.

Once the operation is electronically authorized, any drug introduced through the upper part of the first aid kit (1) will be registered by the input reader (5.1). In specific conditions of designing and labeling the boxes of drugs other data such as the number of tablets or pills each box contains and the expiration date of the drug can be registered.

It is understood that the same operation must be performed to remove any of the drugs contained in the first aid kit; to that end it will be sufficient to key on the keypad (6) and to check in the display (7) that the correct request has been made. The chosen drug is released (the mechanical release system is not an object of this invention) and falls into the drawer (3) due to gravity where it could be removed directly or by drawing out the drawer (3). As the drug passes in front of the output reader (5.2) the corresponding identification and reading is performed deducting the removed unit from the total.

Once one, two or more doses of the corresponding box are consumed, the user will introduce it through the upper part for storage again whereby the input reader (5.1) will add up the existing units and register the new content of the first aid kit (1) in the health card.

The data registered in the health card can logically be known by the family doctor or any other physician who can read the card. This allows knowing the health data of the owner and the content of his/her first aid kit facilitating the issuance of corresponding prescriptions and preventing the prescription of pharmaceutical products already existing in the first aid kit (1). Depending on the actual content of the first aid kit the doctor can prescribe any alternative drug having effects similar to that which he/she may have thought of initially.

The inventor conceives an advanced alternative in which the first aid kit (1) equipped with the control module (8) registering its exact drug content at all times, can be assessable through wireless networks or any other support, such that authorized personnel of the corresponding health organization may know said content accurately to manage it as deemed appropriate to general interest.

Regarding the labeling of boxes of drugs, the need for the rectangular boxes to have labeled thereon the appropriate bar code on the two opposite faces which can be located in front of the input reader (5.1) and output reader (5.2) is understood.

In a simplification of the idea, the inventor considers that an alternative operation of this first aid kit can consist of passing a manual reader by the drug before physically opening the door of the first aid kit passing the reader again as the drug is again stored, but it is understood that system can involve making many mistakes due to the carelessness of the user or even due to a lack of good faith.

In terms of the size of the first aid kit (1) a small first aid kit (1) is envisages for use in private homes by a single user or even families, it being understood that every person must use his/her own health card.

Nevertheless, designing larger first aid kits for use in businesses, industries or factories with many users is not ruled out.

Making the content of this description more extensive so that a person skilled in the art can understand its scope and the advantages derived from the invention, as well as develop and carry the object thereof into practice is not considered necessary.

However, it must be understood that the invention has been described according to a preferred embodiment thereof, therefore it may be susceptible to modifications without involving any alteration of the foundation of said invention, such modifications being able to affect the shape, the size and/or the manufacturing materials; i.e., the terms used in this preferred description of the invention should always be considered in a broad and non-limiting character.

The invention claimed is:

1. An intelligent first aid kit comprising a fixed first aid kit for storing boxes of drugs labeled with bar codes for identification of the drugs, wherein drug input-output flow is vertical from the top towards the bottom, the first aid kit comprising: a parallelepiped container divided into a plurality of elongated compartments with a vertical orientation, having a receiving drawer for drug collection, an output bar code reader in a lower side for automatically identifying the drug when the box passes in front of the bar code reader, a slot for inserting an electronic card, a keypad, a display and a control module, wherein the first aid kit is equipped in an upper side with an input bar code reader for automatically identifying any drug introduced through an upper part of the first aid kit, and wherein the control module is configured for:

automatically registering an exact drug content of the first aid kit at all times by controlling all inputs and outputs of the drugs with information provided by the input bar code reader and the output bar code reader; and recording the drug content of the first aid kit in a microchip of the electronic card inserted in the slot.

2. The intelligent first aid kit according to claim 1, wherein the boxes of drugs are labeled with bar codes containing information with an expiration date of the drug, wherein the control module is further configured for:

automatically registering, through the readings of the input bar code reader, the expiration date of the drugs stored in the first aid kit; and recording the expiration date of the drugs stored in the first aid kit in the microchip of the electronic card inserted in the slot.

3. The intelligent first aid kit according to claim 1, wherein the control module is remotely accessible 'through wireless networks or a support.

* * * * *